US010314961B2

(12) United States Patent
Ishizaki et al.

(10) Patent No.: US 10,314,961 B2
(45) Date of Patent: Jun. 11, 2019

(54) DIALYSATE-EXTRACTING APPARATUS

(71) Applicant: Nikkiso Company Limited, Tokyo (JP)

(72) Inventors: Fumihiko Ishizaki, Shizuoka (JP);
Sumiaki Matsuo, Shizuoka (JP);
Tadashi Iwahori, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 186 days.

(21) Appl. No.: 15/384,993

(22) Filed: Dec. 20, 2016

(65) Prior Publication Data

US 2017/0100530 A1    Apr. 13, 2017

Related U.S. Application Data

(63) Continuation of application No. PCT/JP2015/068561, filed on Jun. 26, 2015.

(30) Foreign Application Priority Data

Jun. 27, 2014   (JP) ................. 2014-133034

(51) Int. Cl.
*A61M 1/14* (2006.01)
*A61M 1/16* (2006.01)
(Continued)

(52) U.S. Cl.
CPC .............. *A61M 1/168* (2013.01); *A61M 1/14* (2013.01); *A61M 1/165* (2014.02); *A61M 1/267* (2014.02);
(Continued)

(58) Field of Classification Search
None
See application file for complete search history.

(56) References Cited

U.S. PATENT DOCUMENTS 5,863,421 A    1/1999 Peter, Jr. et al.
9,192,708 B2    11/2015 Iwahori et al.
(Continued)

FOREIGN PATENT DOCUMENTS

JP    H03073162 A    3/1991
JP    2003093501 A    4/2003
(Continued)

OTHER PUBLICATIONS

Extended European Search Report, Application No. 15811627.7 dated Nov. 8, 2017.
(Continued)

*Primary Examiner* — Chester T Barry
(74) *Attorney, Agent, or Firm* — The Dobrusin Law Firm, PC

(57) ABSTRACT

A dialysate-extracting apparatus is provided in which scattering of dialysate that may occur when an opening-and-closing device is detached from a collecting port can be prevented and the cleanliness of the collecting port can be assuredly maintained. The dialysate-extracting apparatus includes a dialysate-extracting device connected to a dialysate flow route and having a collecting port from which dialysate flowing in the dialysate flow route is collectable, and an opening-and-closing device detachable from and attachable to the dialysate-extracting device in such a manner as to open and close the collecting port and including a seal portion that seals the collecting port in a closed state. When the opening-and-closing device is detached from the dialysate-extracting device, a part of the opening-and-closing device that is on an inner side with respect to the seal portion is bendable and displaceable toward the collecting port.

9 Claims, 15 Drawing Sheets

(51) Int. Cl.
  *A61M 1/26* (2006.01)
  *A61M 1/36* (2006.01)
  *A61M 1/34* (2006.01)
(52) U.S. Cl.
  CPC ......... *A61M 1/3437* (2014.02); *A61M 1/3638* (2014.02); *A61M 2205/3331* (2013.01); *A61M 2205/3337* (2013.01)

(56) References Cited

U.S. PATENT DOCUMENTS

| | | | |
|---|---|---|---|
| 2008/0200837 | A1 | 8/2008 | Frazier et al. |
| 2013/0292313 | A1 | 11/2013 | Fava et al. |
| 2014/0138301 | A1 | 5/2014 | Iwahori et al. |

FOREIGN PATENT DOCUMENTS

| | | |
|---|---|---|
| JP | 2004313522 A | 11/2004 |
| JP | 2009207706 A | 11/2004 |
| JP | 2010184029 A | 8/2010 |
| JP | 2011161060 A | 8/2011 |
| JP | 2013027494 A | 2/2013 |
| JP | 2013027495 A | 2/2013 |
| WO | 2009/074588 A1 | 6/2009 |
| WO | 2013/151114 A1 | 10/2013 |

OTHER PUBLICATIONS

Co-pending U.S. Appl. No. 15/387,913, filed Dec. 22, 2016.
International Search Report from the Japanese Patent Office for Application No. PCT/JP2015/068561, dated Sep. 29, 2015.
Written Opinion from the Japanese Patent Office for Application No. PCT/JP2015/068561, dated Sep. 29, 2015.
Co-pending U.S. Appl. No. 14/163,051, filed Jan. 24, 2014, published as US 2014/0138301.
Co-pending U.S. Appl. No. 14/197,329, filed Mar. 5, 2014, now U.S. Pat. No. 9,192,708.

[Fig 1]
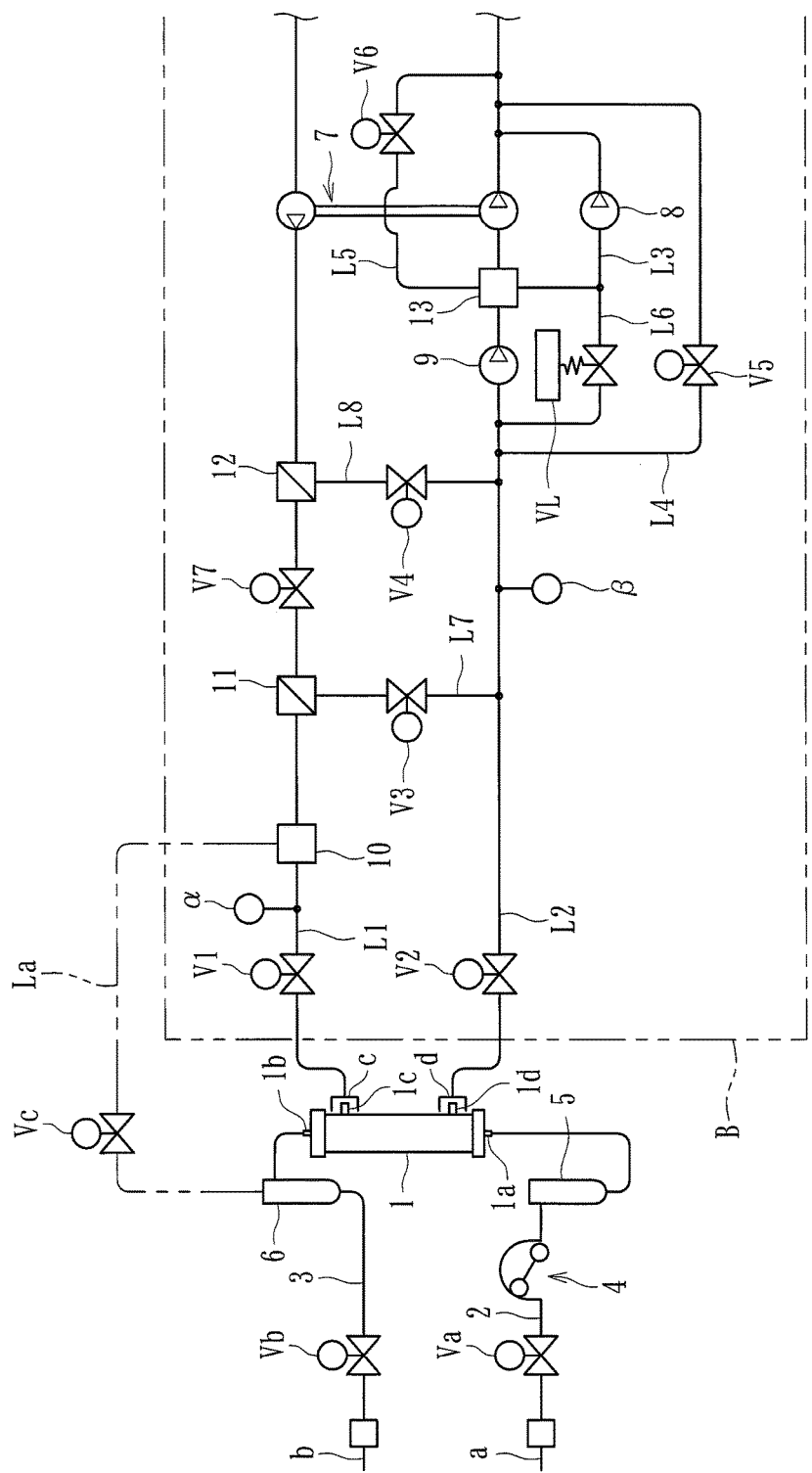

[Fig 2]
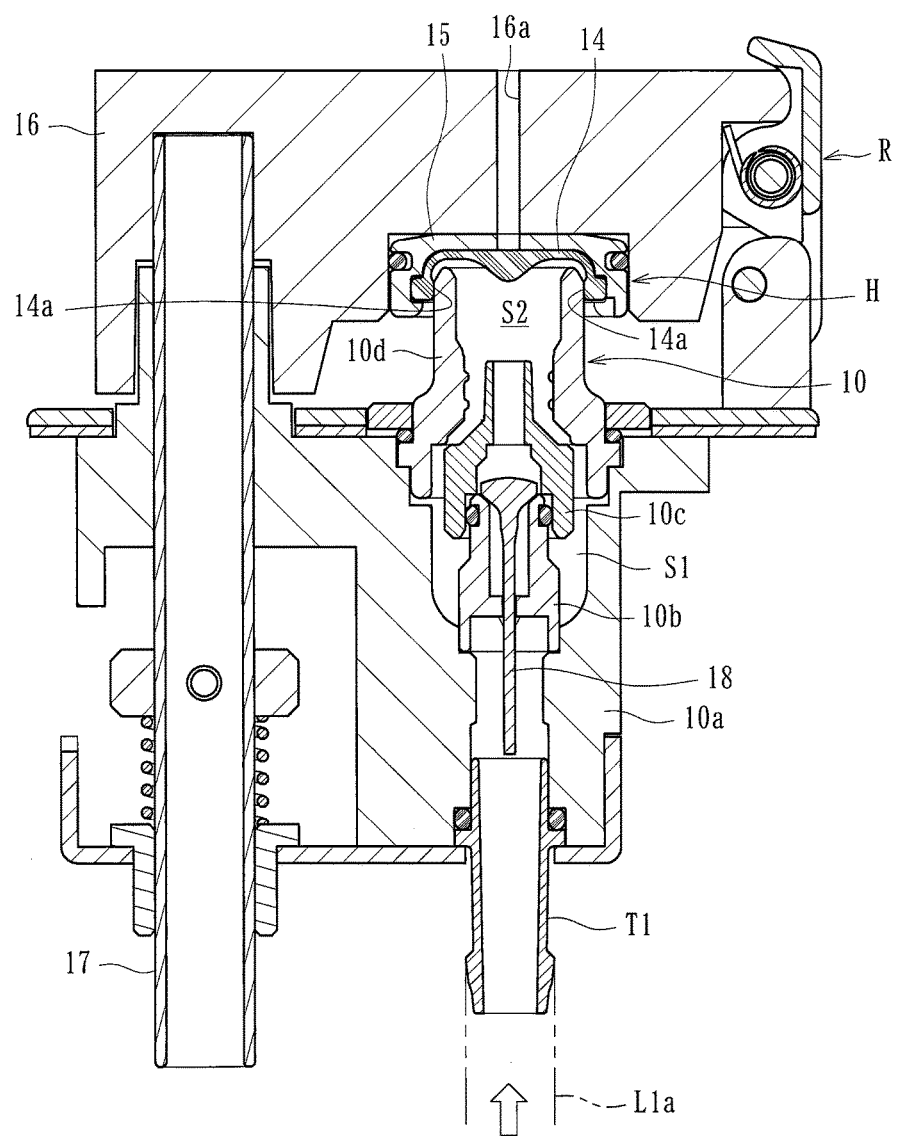

[Fig 3]
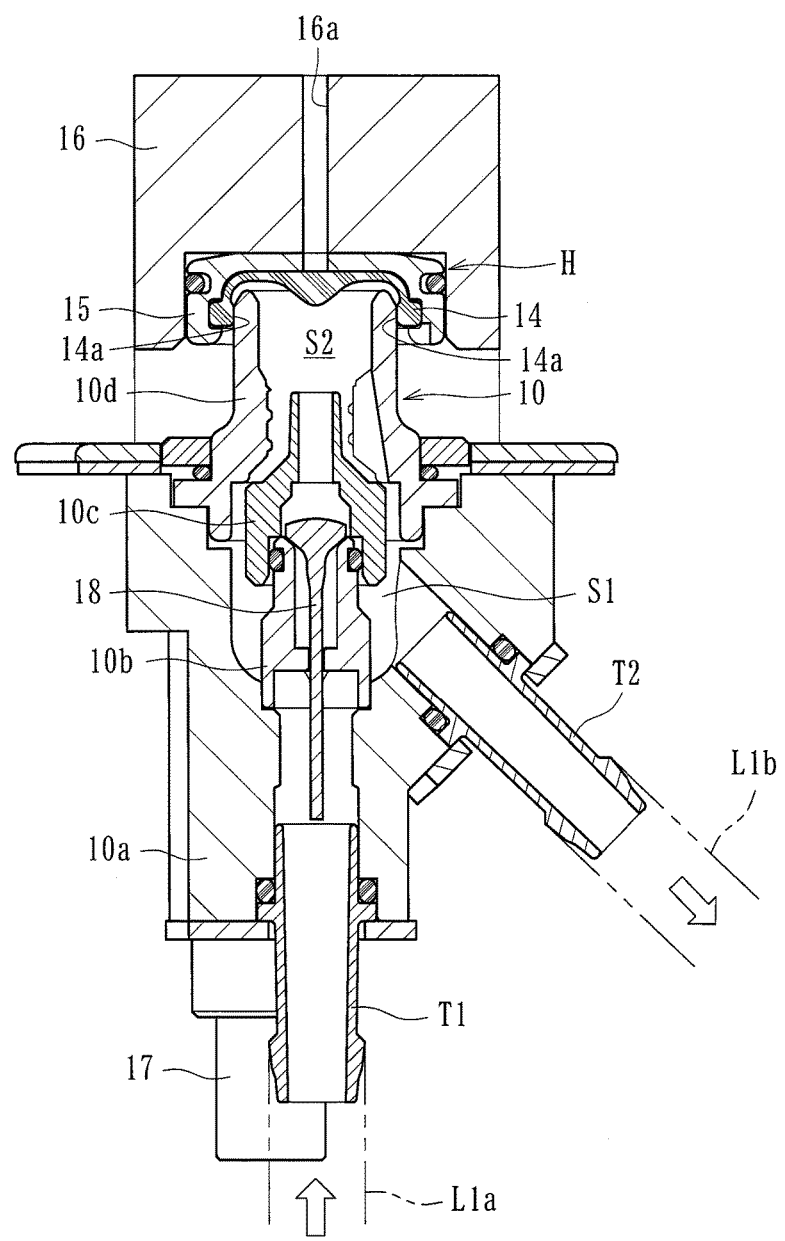

[Fig 4]
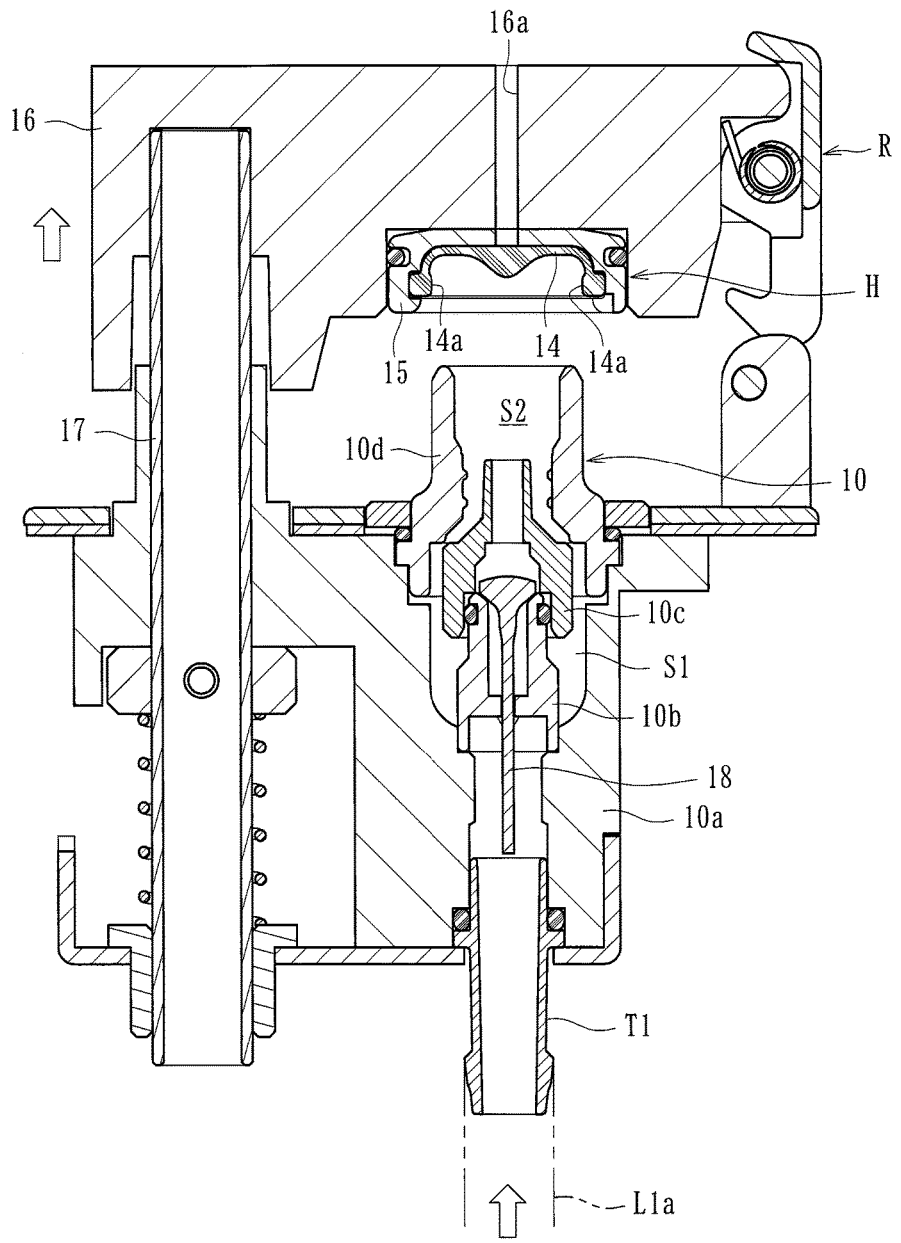

[Fig 5]
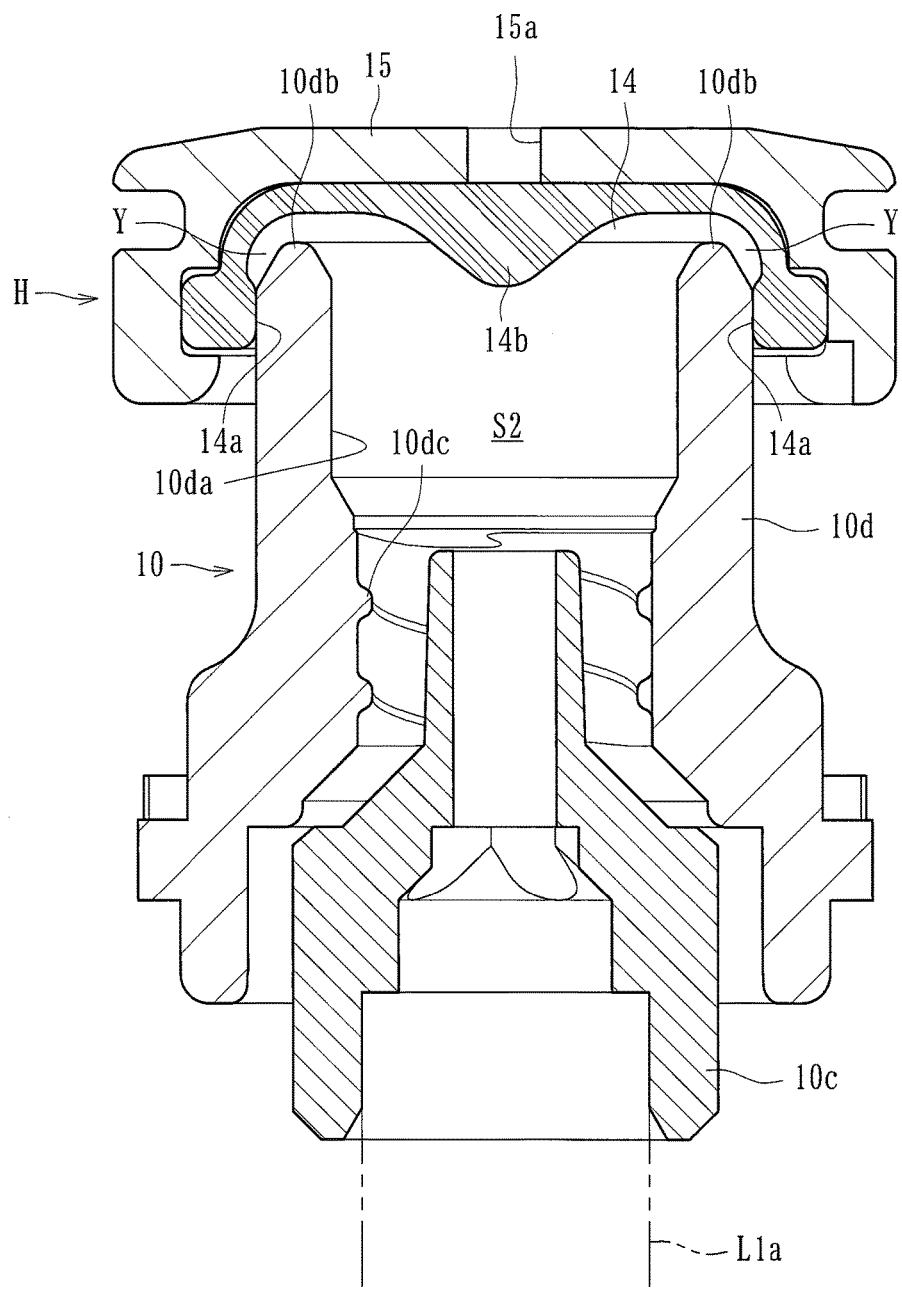

[Fig 6]
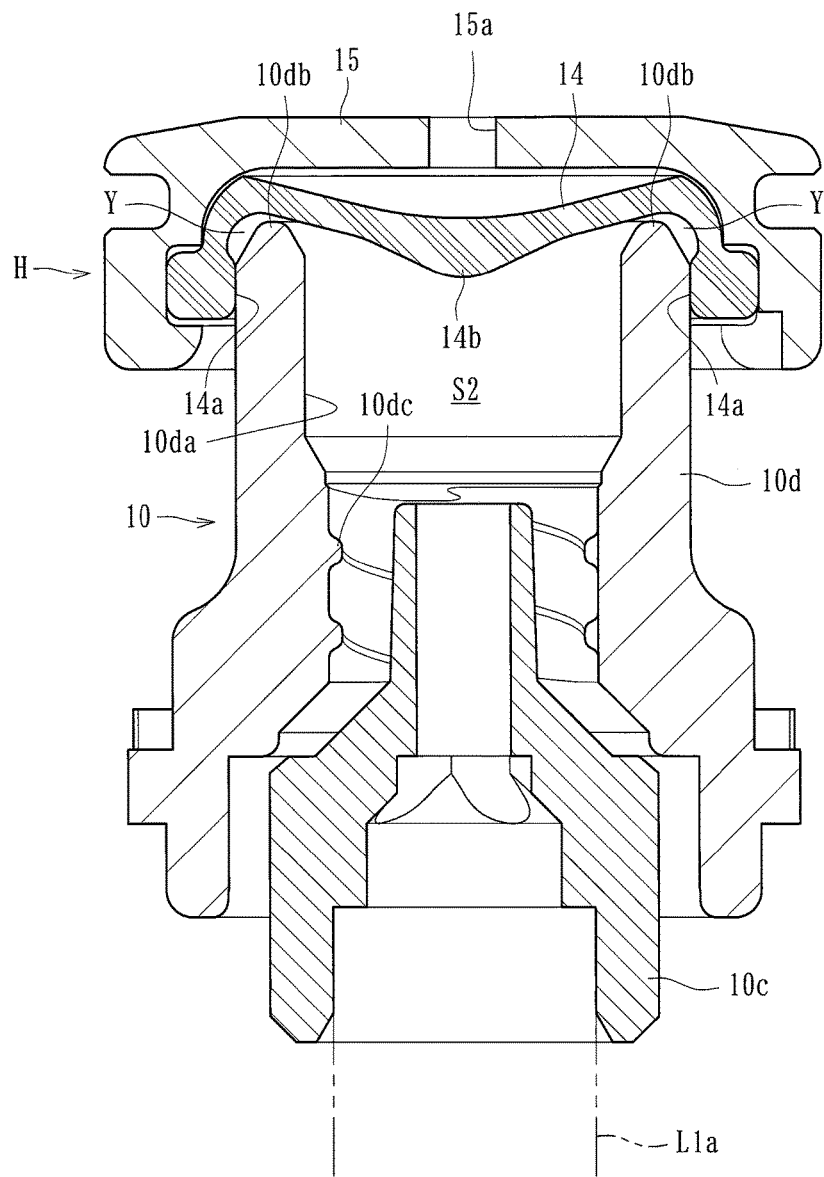

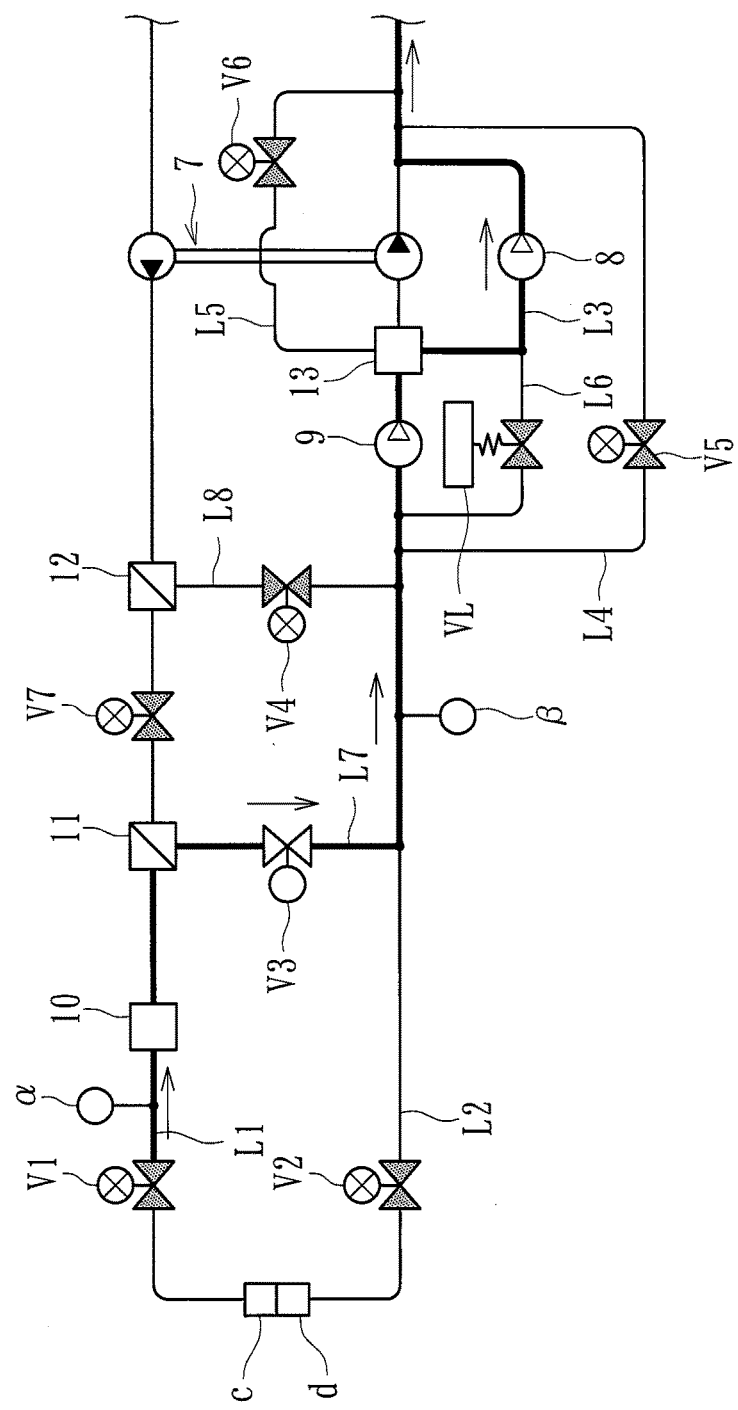
[Fig 7]

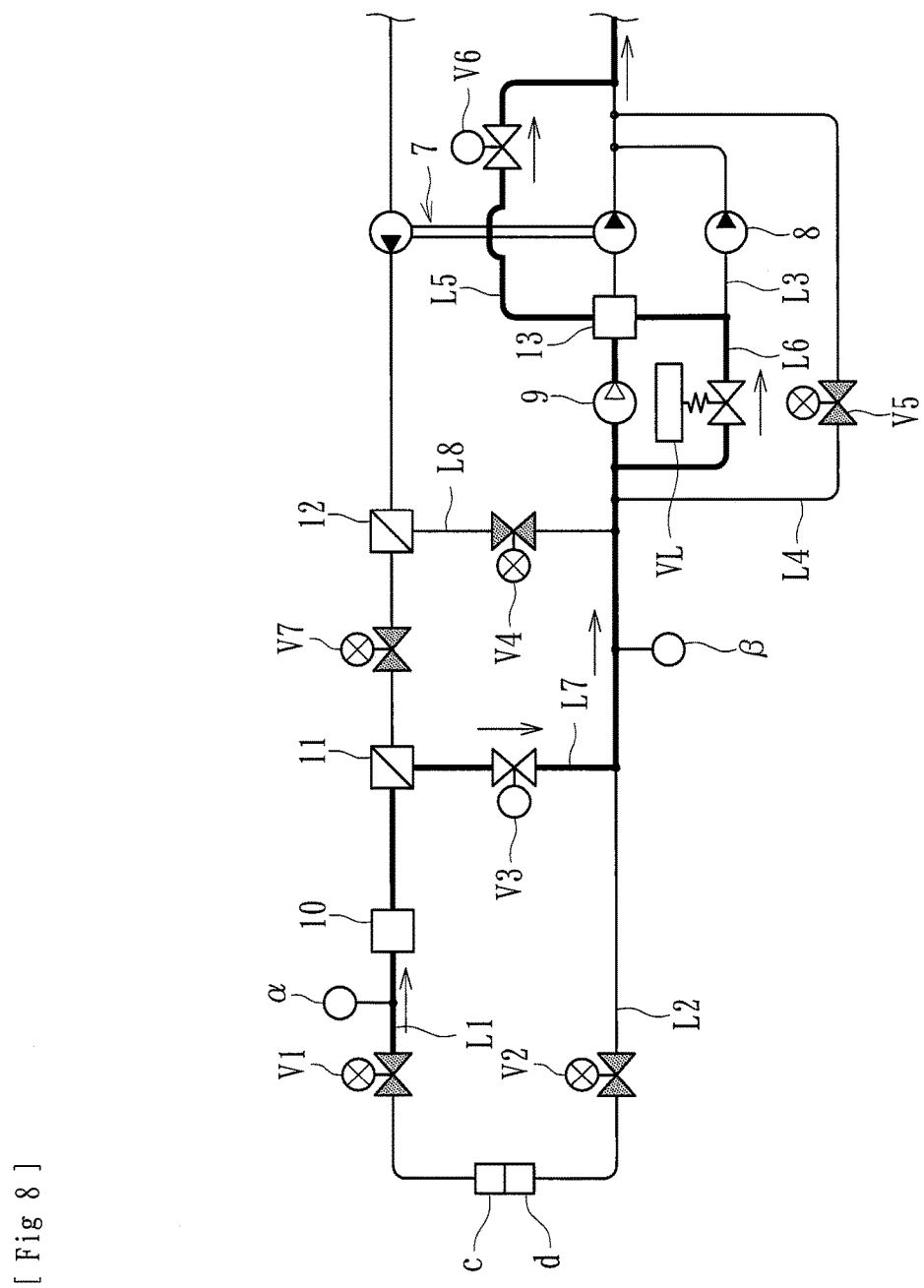
[Fig 8]

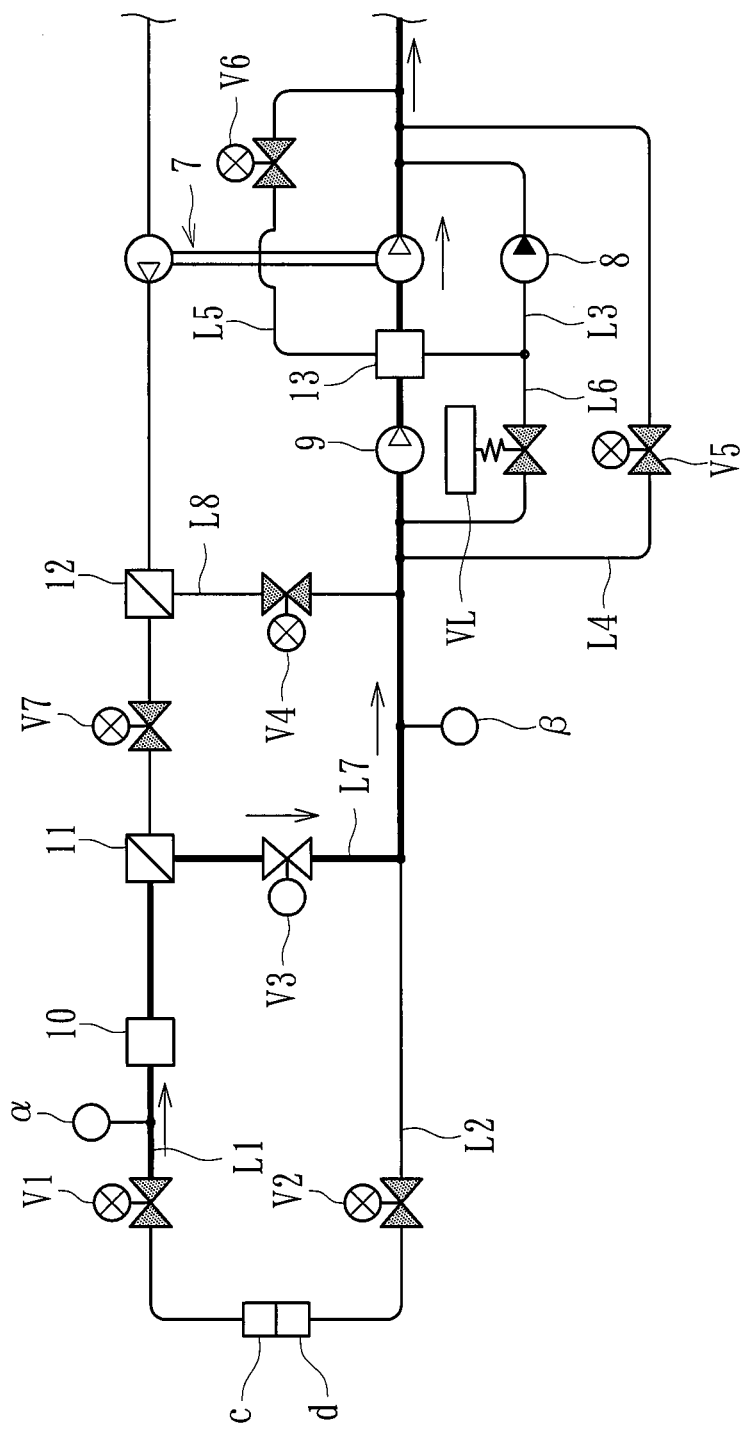
[Fig 9]

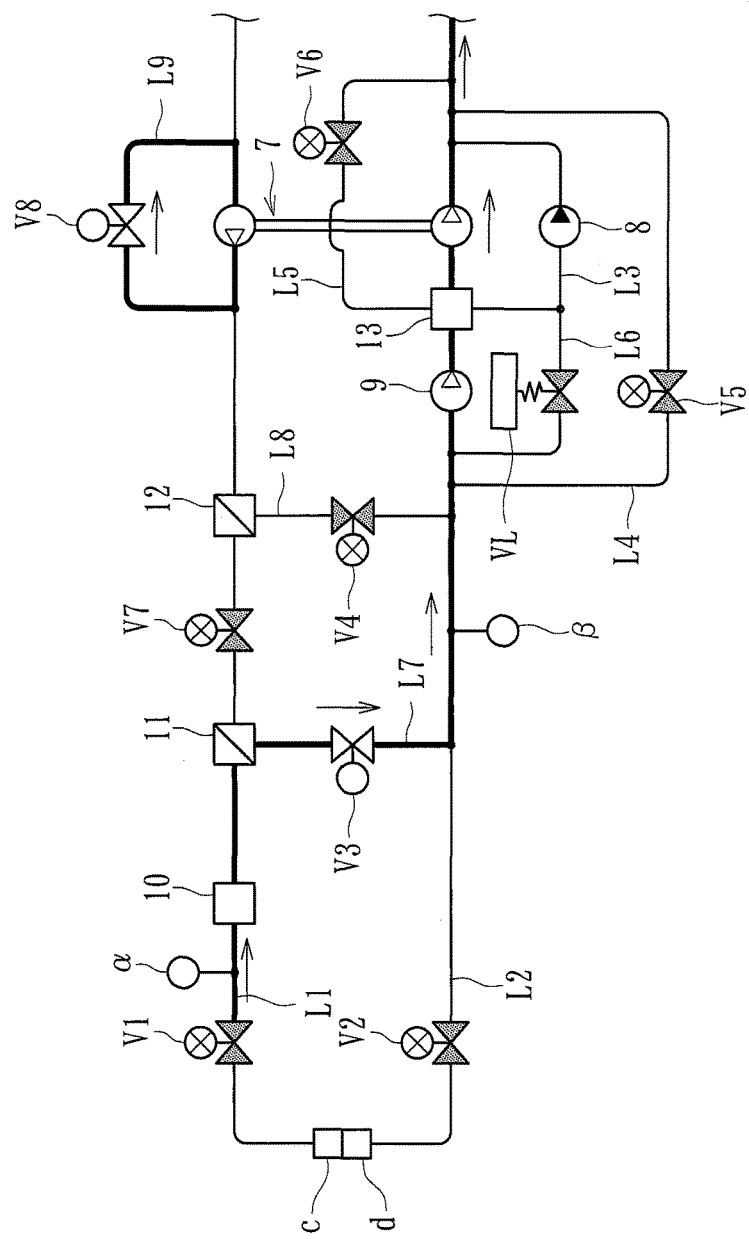
[Fig 10]

[Fig 11]
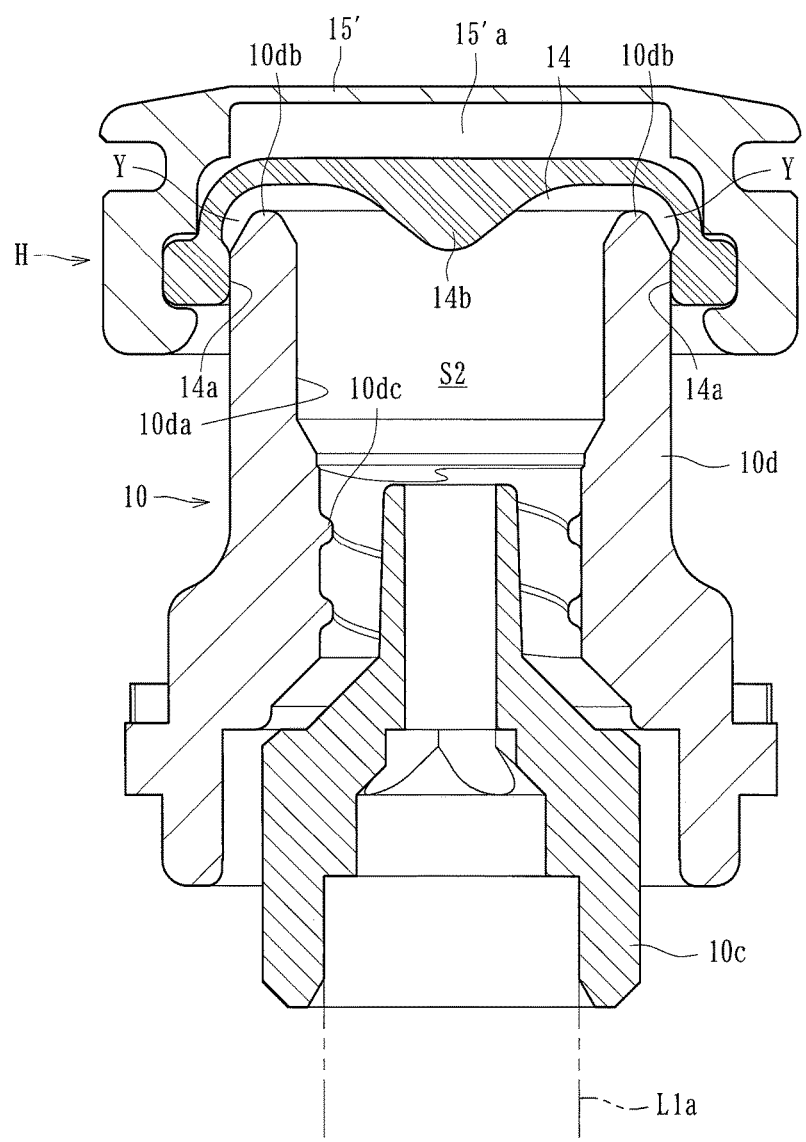

[Fig 12]
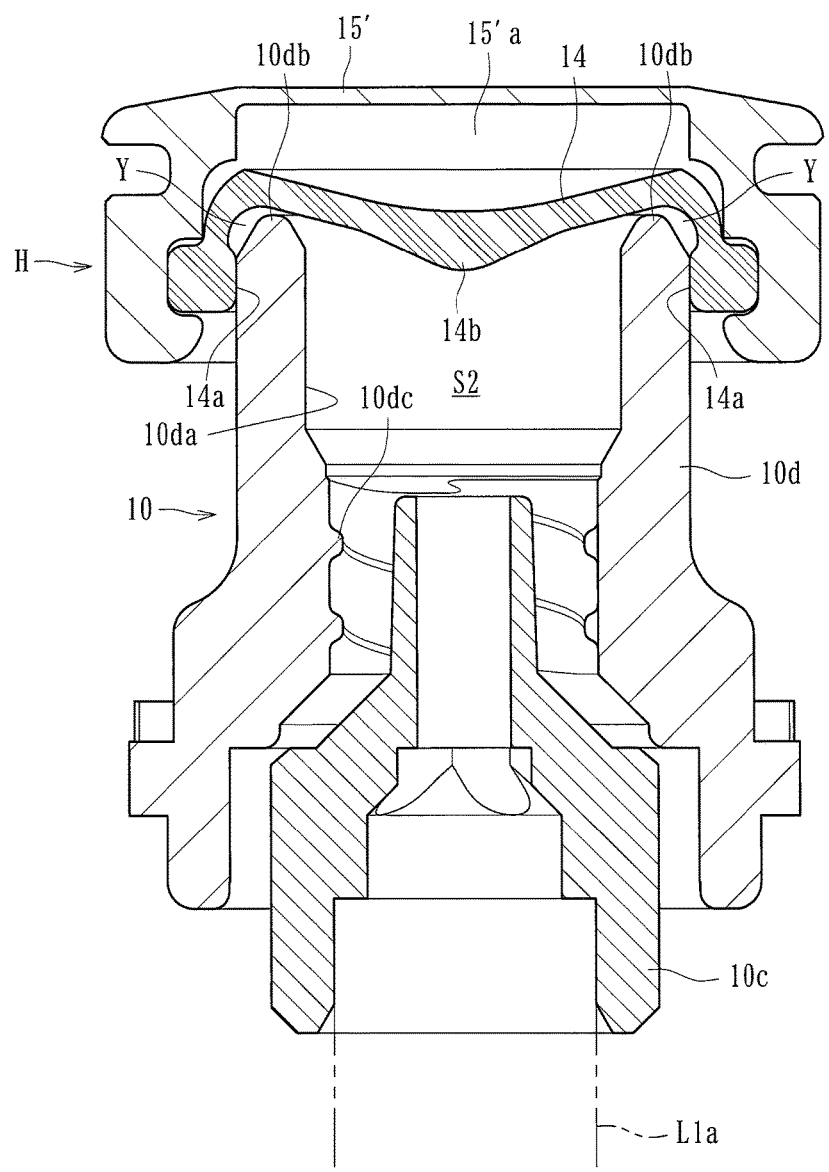

[Fig 13]
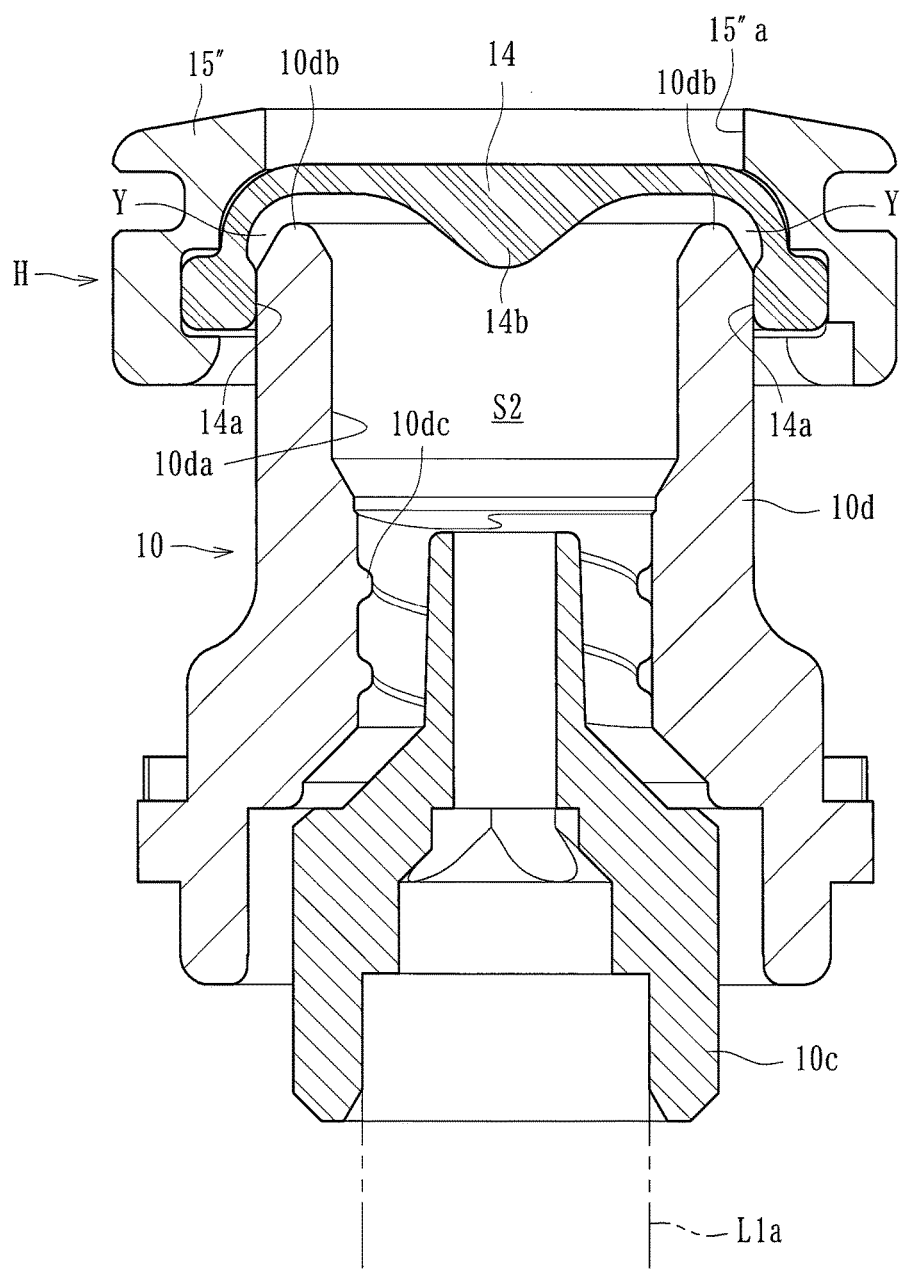

[Fig 14]
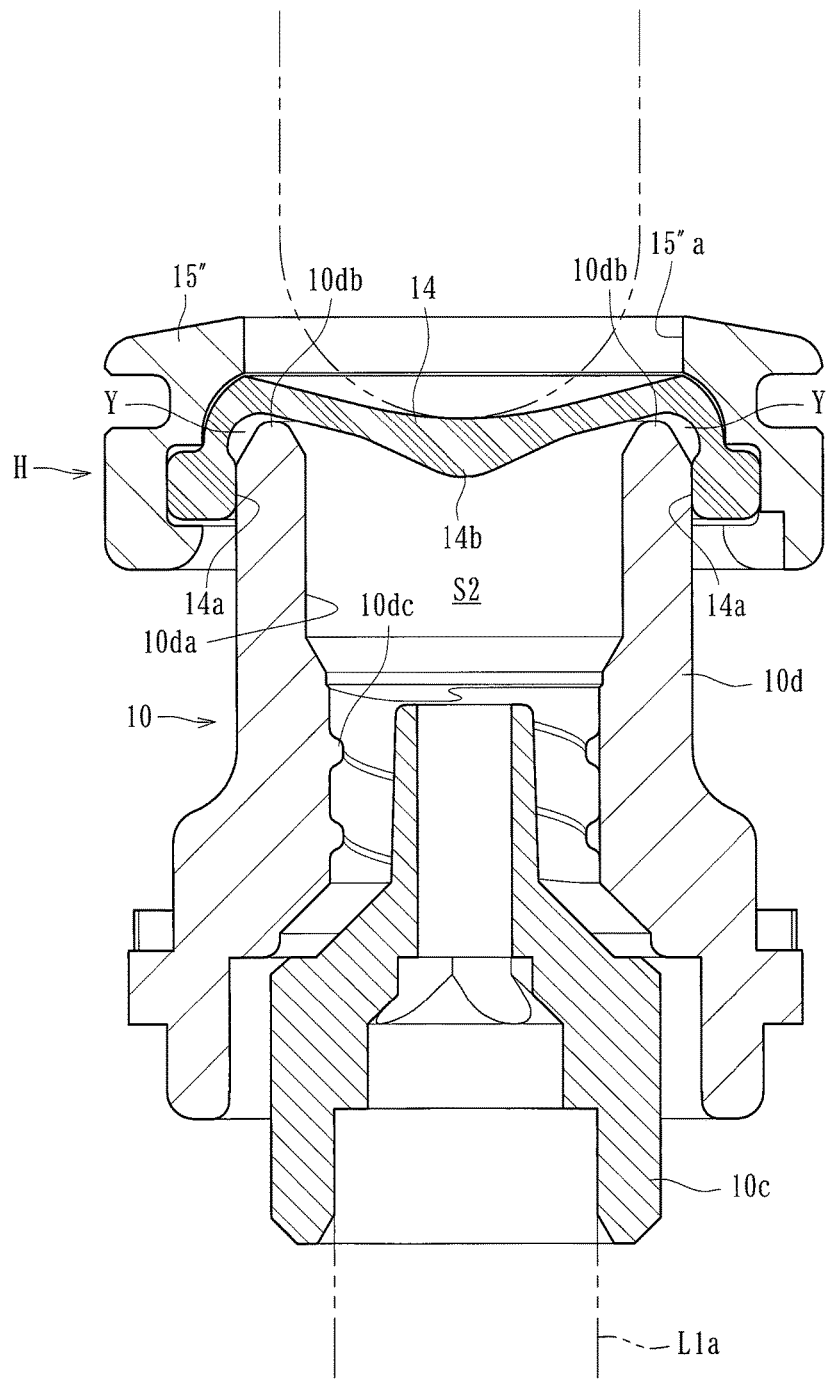

[ Fig 15 ]
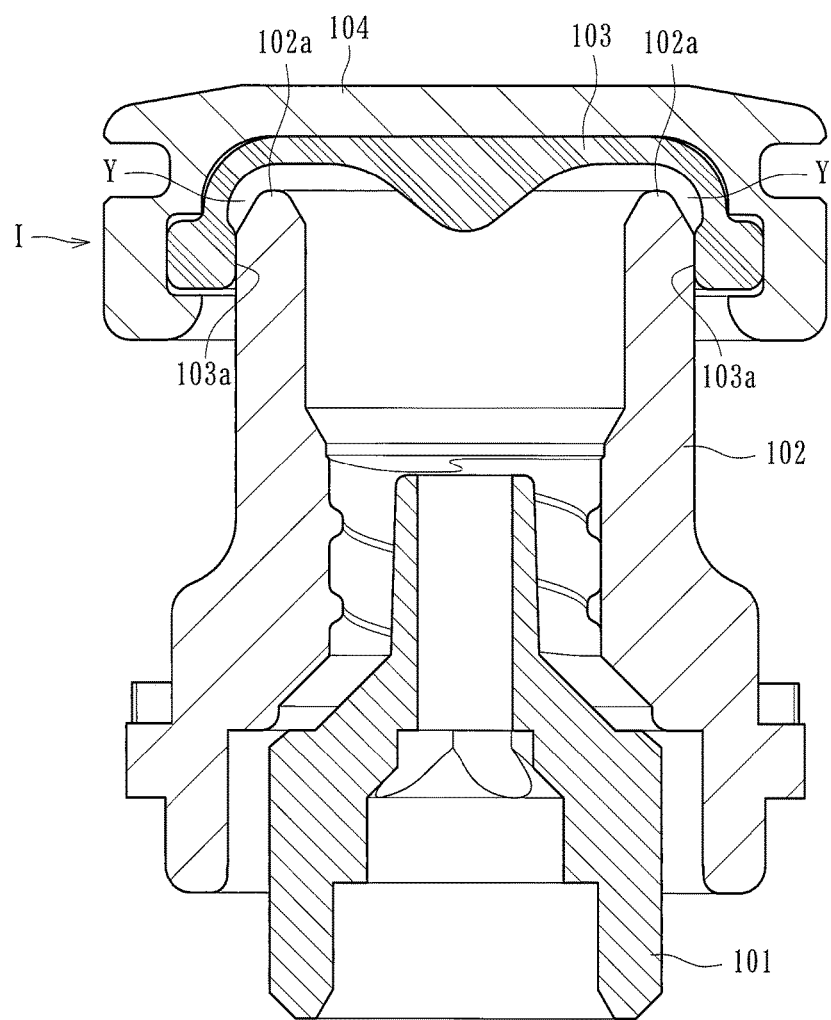

DIALYSATE-EXTRACTING APPARATUS

FIELD

The present invention relates to a dialysate-extracting apparatus including a dialysate-extracting device connected to a dialysate flow route and having a collecting port from which dialysate flowing in the dialysate flow route is collectable, and an opening-and-closing device detachable from and attachable to the dialysate-extracting device in such a manner as to open and close the collecting port and including a seal portion that seals the collecting port in a closed state.

BACKGROUND

Recently, some techniques for dialysis apparatuses serving as blood-purification apparatuses have been proposed, such as a technique of performing priming, blood returning, or substitution (emergency fluid infusion) by using dialysate to be supplied to a dialyzer when dialysis treatment (particularly, on-line HDF or on-line HF) is given, and a technique of using the dialysate as substitution fluid for the treatment of on-line HDF or on-line HF. For example, a dialysis apparatus is disclosed by PTL 1 that includes a dialysate-supplying line having one end connected to a dialysate-extracting port (hereinafter referred to as "collecting port") provided at a predetermined position of a dialysate-introducing line and the other end connected to a blood circuit (an arterial blood circuit or a venous blood circuit), and a substitution pump provided for supplying the dialysate. With such a dialysis apparatus, when priming, blood returning, or substitution (emergency fluid infusion) is performed, the dialysate in the dialysate-introducing line can be supplied to the blood circuit (the arterial blood circuit or the venous blood circuit) by activating the substitution pump.

Typically, as illustrated in FIG. 15, the collecting port is provided with an opening-and-closing device I that is detachable therefrom and attachable thereto. The opening-and-closing device I is detached from a collecting port 102, and a substitution line or the like is connected thereto. If the substitution line or the like is not connected, the opening-and-closing device I is attached to the collecting port 102 so that the dialysate flowing in the dialysate-introducing line does not leak to the outside. The opening-and-closing device I is provided with a seal member 103 and a cap member 104 that are fixed therein. With the opening-and-closing device I attached to the collecting port 102, a seal portion 103a of the seal member 103 is in contact with the collecting port 102 and can seal the collecting port 102.

The collecting port 102 is provided thereinside with an introducing member 101 into which the dialysate is introduced. With the opening-and-closing device I attached, when fluid such as a cleaning solution or a disinfecting solution is introduced from the dialysate-introducing line through the introducing member 101, the fluid collides with the opening-and-closing device I and flows backward (downward in FIG. 15). Then, the fluid is allowed to flow through the gap between the outer peripheral surface of the introducing member 101 and the inner peripheral surface of the collecting port 102 into the dialysate-introducing line. In such a process, it is preferable to allow the cleaning solution and the disinfecting solution to reach a top end 102a of the collecting port 102 so that the top end 102a is cleaned and disinfected. Therefore, the seal portion 103a of the seal member 103 is configured to come into contact with the outer peripheral wall of the collecting port 102 and seal the collecting port 102.

CITATION LIST

Patent Literature

PTL 1: Japanese Unexamined Patent Application Publication No. 2004-313522.

SUMMARY

In the above known dialysate-extracting apparatus, however, since the seal portion 103a of the seal member 103 is configured to come into contact with the outer peripheral wall of the collecting port 102 and seal the collecting port 102 so that the top end 102a of the collecting port 102 is cleaned and disinfected, a space Y is provided, with the opening-and-closing device I attached, between the top end 102a of the collecting port 102 and the seal portion 103a, allowing the dialysate to stay in the space Y. If the opening-and-closing device I is detached from the collecting port 102 in such a state, the dialysate in the space Y may scatter to the outside. Such a situation is not preferable in terms of hygiene.

In view of the above circumstances, the present invention provides a dialysate-extracting apparatus in which scattering of dialysate that may occur when an opening-and-closing device is detached from a collecting port can be prevented and the cleanliness of the collecting port can be assuredly maintained.

The teachings herein provide a dialysate-extracting apparatus that includes a dialysate-extracting device connected to a dialysate flow route and having a collecting port from which dialysate flowing in the dialysate flow route is collectable; and an opening-and-closing device detachable from and attachable to the dialysate-extracting device in such a manner as to open and close the collecting port and including a seal portion that seals the collecting port in a closed state, wherein the opening-and-closing device is detached from the dialysate-extracting device, a part of the opening-and-closing device that is on an inner side with respect to the seal portion is bendable and displaceable toward the collecting port.

The teachings herein provide the dialysate-extracting apparatus taught herein, wherein the opening-and-closing device includes a seal member that is a flexible member, a part of which forms the seal portion; and a cap member that covers and holds the seal member, and wherein a part of the seal member that is on the inner side with respect to the seal portion is bendable and displaceable toward the collecting port.

The teachings herein provide the dialysate-extracting apparatus taught herein, wherein the cap member has an introduction hole that allows outside air to be introduced into a gap between the cap member and the seal member when the seal member is bent and displaced toward the collecting port.

The teachings herein provide the dialysate-extracting apparatus taught herein, wherein the cap member has a space provided between the cap member and the seal member and that allows the seal member to be bendable and displaceable toward the collecting port.

The teachings herein provide the dialysate-extracting apparatus taught herein, wherein, when the opening-and-closing device is detached from the dialysate-extracting device, the part of the opening-and-closing device that is on the inner side with respect to the seal portion is bendable and displaceable toward the collecting port by reducing a volume of fluid in the dialysate flow route to which the dialysate-extracting device is connected.

The teachings herein provide the dialysate-extracting apparatus taught herein, wherein the cap member has an opening through which the seal member is allowed to be pushed, and the seal member is bendable and displaceable toward the collecting port through the opening.

According to the teachings herein, when the opening-and-closing device is detached from the dialysate-extracting device, the part thereof on the inner side with respect to the seal portion is bendable and displaceable toward the collecting port. Therefore, scattering of the dialysate that may occur when the opening-and-closing device is detached from the collecting port can be prevented, and the cleanliness of the collecting port can be assuredly maintained.

According to the teachings herein, the opening-and-closing device includes the seal member that is a flexible member, a part of which forms the seal portion; and the cap member that covers and holds the seal member. Furthermore, the part of the seal member that is on the inner side with respect to the seal portion is bendable and displaceable toward the collecting port. Therefore, while the sealing with the seal member and the displacement of the seal member are smoothly achieved, the detaching from and attaching to the collecting port of the dialysate-extracting device can be made easy by the cap member.

According to the teachings herein, the cap member has the introduction hole that allows the outside air to be introduced into the gap between the cap member and the seal member when the seal member is bent and displaced toward the collecting port. Therefore, the seal member can be bent more smoothly and assuredly.

According to the teachings herein, the cap member has the space provided between the cap member and the seal member and that allows the seal member to be bendable and displaceable toward the collecting port. Therefore, the seal member can be bent smoothly and assuredly without providing any hole or the like in the cap member.

According to the teachings herein, when the opening-and-closing device is detached from the dialysate-extracting device, the part of the opening-and-closing device that is on the inner side with respect to the seal portion is bendable and displaceable toward the collecting port by reducing the volume of the fluid in the dialysate flow route to which the dialysate-extracting device is connected. Therefore, the seal member can be assuredly bent and displaced toward the collecting port at an arbitrary timing before the opening-and-closing device is detached.

According to the teachings herein, the cap member has the opening through which the seal member is allowed to be pushed, and the seal member is bendable and displaceable toward the collecting port through the opening. Therefore, the seal member can be bent and displaced toward the collecting port at an arbitrary timing.

BRIEF DESCRIPTION OF DRAWINGS

FIG. 1 is a schematic diagram of a blood-purification apparatus to which a dialysate-extracting apparatus according to the present invention is applied.

FIG. 2 is a schematic sectional view of a dialysate-extracting apparatus (with an opening-and-closing device attached to a collecting port) according to a first embodiment of the present invention.

FIG. 3 is another schematic sectional view of the dialysate-extracting apparatus (with the opening-and-closing device attached to the collecting port).

FIG. 4 is a schematic sectional view of a dialysate-extracting device included in the dialysate-extracting apparatus (with the opening-and-closing device detached from the collecting port).

FIG. 5 is a schematic sectional view of the dialysate-extracting apparatus with the opening-and-closing device attached to the collecting port and in a state before a seal member is bent.

FIG. 6 is a schematic sectional view of the dialysate-extracting apparatus with the opening-and-closing device attached to the collecting port and in a state after the seal member is bent.

FIG. 7 is a piping diagram illustrating an operation of bending the seal member of the dialysate-extracting apparatus (by using an ultrafiltration pump).

FIG. 8 is a piping diagram illustrating an operation of bending the seal member of the dialysate-extracting apparatus (by using a pressurizing pump).

FIG. 9 is a piping diagram illustrating an operation of bending the seal member of the dialysate-extracting apparatus (by using a fluid-delivering pump).

FIG. 10 is another piping diagram illustrating the operation of bending the seal member of the dialysate-extracting apparatus (by using the fluid-delivering pump).

FIG. 11 is a schematic sectional view of a dialysate-extracting apparatus (before a seal member is bent) according to a second embodiment of the present invention.

FIG. 12 is a schematic sectional view of the dialysate-extracting apparatus (after the seal member is bent).

FIG. 13 is a schematic sectional view of a dialysate-extracting apparatus (before a seal member is bent) according to a third embodiment of the present invention.

FIG. 14 is a schematic sectional view of the dialysate-extracting apparatus (after the seal member is bent).

FIG. 15 is a schematic sectional view of a known dialysate-extracting apparatus.

DETAILED DESCRIPTION

Embodiments of the present invention will now be described specifically with reference to the drawings.

A dialysate-extracting apparatus according to the present embodiment is provided to a blood-purification apparatus used for blood-purification treatment (blood dialysis treatment) and can collect dialysate. As illustrated in FIG. 1, the applicable blood-purification apparatus basically includes a blood circuit in which an arterial blood circuit 2 and a venous blood circuit 3 are connected to a dialyzer 1 (a blood-purification device), and a dialysis-apparatus body B including a dialysate-introducing line L1 and a dialysate-discharging line L2.

The dialyzer 1 is intended for purifying blood and is connected to the arterial blood circuit 2 and the venous blood circuit 3, which are included in the blood circuit, with respective ports 1a and 1b interposed therebetween. The dialyzer 1 is also connected to the dialysate-introducing line L1 and the dialysate-discharging line L2 with respective ports 1c and 1d interposed therebetween. The arterial blood circuit 2 is provided with a blood pump 4, which is a peristaltic pump. When the blood pump 4 is activated, fluid such as blood can be delivered into the blood circuit.

An arterial puncture needle (a) and a venous puncture needle (b) are attachable to the distal end of the arterial blood circuit 2 and the distal end of the venous blood circuit 3, respectively. When the blood pump 4 is activated with the arterial puncture needle (a) and the venous puncture needle (b) stuck in a patient, the blood of the patient that is collected from the arterial puncture needle (a) extracorporeally circulates through the blood circuit. After the blood is purified and ultrafiltered by the dialyzer 1, the blood is returned to the patient from the venous puncture needle (b). The arterial blood circuit 2 is provided with an air-trapping chamber 5 and with a clamping device Va on the distal side thereof. The venous blood circuit 3 is provided with an air-trapping chamber 6 and with a clamping device Vb on the distal side thereof.

Furthermore, the dialysate-introducing line L1 and the dialysate-discharging line L2 are provided with a duplex pump 7 serving as a fluid-delivering pump that supplies the dialysate prepared to have a predetermined concentration to the dialyzer 1 and discharges the dialysate from the dialyzer 1. That is, the duplex pump 7 is provided over the dialysate-introducing line L1 and the dialysate-discharging line L2 such that, when the duplex pump 7 is activated, the dialysate is introduced into the dialyzer 1 through the dialysate-introducing line L1 and is discharged from the dialyzer 1 through the dialysate-discharging line L2.

The dialysate-introducing line L1 is provided with filters 11 and 12. The dialysate to be introduced into the dialyzer 1 can be filtered by the filters 11 and 12. Furthermore, the flow route is closable and openable at an arbitrary timing by each of electromagnetic valves V1 and V7. The dialysate-introducing line L1 is further provided with a pressure-detecting device α on the upstream side with respect to the electromagnetic valve V1 (between the electromagnetic valve V1 and a dialysate-extracting device 10). The pressure-detecting device (a) is a sensor capable of detecting the pressure inside the flow route (the fluid pressure in the flow route). The dialysate-introducing line L1 is connected to the dialysate-discharging line L2 with bypass lines L7 and L8. The bypass lines L7 and L8 are provided with electromagnetic valves V3 and V4, respectively.

The dialysate-discharging line L2 is provided with detour lines L3 and L4 that detour the duplex pump 7. The detour line L3 is provided with an ultrafiltration pump 8. Hence, when the ultrafiltration pump 8 is activated in the process of extracorporeally circulating the blood of the patient through the blood circuit, the blood flowing in the dialyzer 1 can be ultrafiltered so that water is removed therefrom. The dialysate-discharging line L2 is further provided with a pressurizing pump 9 on the upstream side (on the left side in the drawing) with respect to the duplex pump 7. The pressurizing pump 9 adjusts the fluid pressure in a portion of the dialysate-discharging line L2 that is located in the duplex pump 7 (a fluid-delivering pump). The dialysate-discharging line L2 is also provided with a detour line L5 extending from a point between the pressurizing pump 9 and the duplex pump 7 and with a chamber 13 interposed therebetween.

The dialysate-discharging line L2 is further provided with a pressure-detecting device β on the downstream side with respect to an electromagnetic valve V2 (between the connection with the bypass line L7 and the connection with the bypass line L8). The pressure-detecting device β is a sensor capable of detecting the pressure inside the flow route (the fluid pressure in the flow route). Furthermore, the dialysate-discharging line L2 and the detour lines L4 and L5 branching off therefrom are provided with respective electromagnetic valves V2, V5, and V6, with each of which the flow route is closable and openable at an arbitrary timing. The dialysate-discharging line L2 is also provided with a detour line L6 extending from a point between the connection with the detour line L4 and the pressurizing pump 9 to the detour line L3. The detour line L6 is provided with a relief valve VL.

The dialysate-introducing line L1 according to the present embodiment is provided with a dialysate-extracting apparatus capable of collecting the dialysate flowing in the dialysate-introducing line L1. As illustrated in FIGS. 2 to 4, the dialysate-extracting apparatus includes the dialysate-extracting device 10 connected to the dialysate flow route (the dialysate-introducing line L1) and having a collecting port 10d from which the dialysate flowing in the dialysate flow route is collectable, and an opening-and-closing device H detachable from and attachable to the dialysate-extracting device 10 in such a manner as to open and close the collecting port 10d and including a seal portion 14a that seals the collecting port 10d in the closed state.

The dialysate-extracting device 10 includes a first extracting member 10a connected to the dialysate-introducing line L1, a second extracting member 10b provided in the first extracting member 10a, a third extracting member 10c attached to the second extracting member 10b and having a flow route therein, and the collecting port 10d provided over the third extracting member 10c. The collecting port 10d is a port-shaped member to which one end of a dialysate-supplying line La (see FIG. 1) is connected. As illustrated in FIGS. 5 and 6, the collecting port 10d has an insertion hole 10da into which a connector (not illustrated) provided at the one end of the dialysate-supplying line La is inserted, a top end 10db, and a female screw portion 10dc with which the connector is meshable. The collecting port 10d is detachable from the connector.

The dialysate-supplying line La is connected to the collecting port 10d of the dialysate-extracting device 10 at the one end thereof and to the blood circuit (the air-trapping chamber 6 connected to the venous blood circuit 3 in the present embodiment) at the other end thereof, thereby providing a flow route through which the dialysate in the dialysate-introducing line L1 can be supplied to the blood circuit. The dialysate-supplying line La is provided with a clamping device Vc. The clamping device Vc is openable and closable at an arbitrary timing. In the present embodiment, the other end of the dialysate-supplying line La is connected to the air-trapping chamber 6. Alternatively, the other end of the dialysate-supplying line La may be connected to another element (for example, the air-trapping chamber 5 connected to the arterial blood circuit 2, or the like) of the blood circuit.

The first extracting member 10a of the dialysate-extracting device 10 according to the present embodiment has an introduction port T1 and a discharge port T2, to which an introduction end L1a and a discharge end L1b of the dialysate-introducing line L1 are connected, respectively. The second extracting member 10b and the third extracting member 10c each have thereinside a fluid flow route communicating with the introduction port T1. The flow route is provided with a check valve 18. The check valve 18 allows the fluid to flow from the dialysate-supplying line La toward the blood circuit (the flow toward the upper side in FIGS. 2 and 4) but stops the fluid from flowing from the blood circuit toward the dialysate-introducing line L1 (the flow toward the lower side in the same drawings).

The tip of the third extracting member 10c is open in the collecting port 10d. Therefore, the fluid flowing in the flow route passing through the second extracting member 10b and the third extracting member 10c is allowed to reach the inside of the collecting port 10d. A space S2 in which the fluid can flow is provided between the third extracting member 10c and the opening-and-closing device H. The space S2 communicates with a space S1 provided in the first extracting member 10a. That is, a gap of a predetermined size is provided between the outer peripheral surface of the third extracting member 10c and the inner peripheral surface of the collecting port 10d, and the gap allows the space S1 and the space S2 to communicate with each other.

The space S2 is connected to the discharge port T2, and the fluid in the space S2 flows into the dialysate-introducing line L1 through the discharge port T2. Hence, with the opening-and-closing device H detached from the dialysate-extracting device 10, the dialysate introduced from the introduction port T1 is discharged from the collecting port 10d through the flow route passing through the second extracting member 10b and the third extracting member 10c and is supplied to the blood circuit through the dialysate-supplying line La. On the other hand, with the opening-and-closing device H attached to the dialysate-extracting device 10, the dialysate introduced from the introduction port T1 flows into the spaces S2 and S1 and returns to the dialysate-introducing line L1 through the discharge port T2.

The opening-and-closing device H according to the present embodiment includes a seal member 14 that is a flexible member made of a material such as resin or rubber and a part of which forms the seal portion 14a; and a cap member 15 that covers and holds the seal member 14 and is made of a material such as hard resin. The opening-and-closing device H is a combination of the seal member 14 and the cap member 15. The seal member 14 includes the seal portion 14a at the edge thereof. The seal portion 14a seals the collecting port 10d by coming into contact with the outer peripheral surface of the collecting port 10d.

With the opening-and-closing device H attached to the collecting port 10d, the seal member 14 prevents the dialysate flowing in the dialysate-introducing line L1 from leaking to the outside and allows the cleaning solution or the disinfecting solution flowing in the dialysate-introducing line L1 to reach the top end 10db of the collecting port 10d. Thus, the top end 10db and a part therearound (including a part facing a space Y produced between the seal portion 14a and the top end 10db) can be cleaned or disinfected. The seal member 14 has a projection 14b provided at the center of a surface thereof facing the collecting port 10d. The projection 14b projects toward the collecting port 10d.

As illustrated in FIGS. 2 and 4, the opening-and-closing device H according to the present embodiment is held by a lid member 16 attached to a shaft member 17 that is vertically movable. When the lid member 16 is lifted upward, the opening-and-closing device H is detached from the dialysate-extracting device 10 as illustrated in FIG. 4. When the lid member 16 is pushed downward, the opening-and-closing device H is attached to the dialysate-extracting device 10 as illustrated in FIG. 2. The lid member 16 has a through hole 16a provided in correspondence with an introduction hole 15a of the cap member 15. Reference numeral R in the drawings denotes a locking device that locks the lid member 16 with the opening-and-closing device H attached to the dialysate-extracting device 10.

When the opening-and-closing device H according to the present embodiment is detached from the dialysate-extracting device 10, a part of the seal member 14 that is on the inner side with respect to the seal portion 14a is bendable and displaceable toward the collecting port 10d. That is, when (before) the opening-and-closing device H is detached from the dialysate-extracting device 10, the seal member 14 in the state illustrated in FIG. 5 is elastically deformed and bent, whereby the part on the inner side with respect to the seal portion 14a can be displaced toward the collecting port 10d as illustrated in FIG. 6.

Thus, since the seal member 14 is bent and is displaced toward the collecting port 10d, the volume of the space S2 is reduced by the amount of displacement. Furthermore, the dialysate in the space Y between the seal portion 14a of the seal member 14 and the top end 10db of the dialysate-extracting device 10 is pushed into the space S2 in the insertion hole 10da. After that, if the opening-and-closing device H is detached from the collecting port 10d, the dialysate having been in the space Y does not scatter to the outside, and the dialysate in the space S2 can be prevented from leaking to the outside.

Particularly, the cap member 15 according to the present embodiment has the introduction hole 15a through which the outside air can be introduced into a gap between the cap member 15 and the seal member 14 when the seal member 14 is bent and displaced toward the collecting port 10d. The lid member 16 (see FIGS. 2 and 3) according to the present embodiment has the through hole 16a at the position corresponding to the introduction hole 15a. Therefore, the outside air can be introduced into the gap between the cap member 15 and the seal member 14. Hence, while the sealing with the seal member 14 and the displacement of the seal member 14 are smoothly achieved, detaching and attaching the opening-and-closing device H from and to the collecting port 10d of the dialysate-extracting device 10 can be made easy by the cap member 15. When the seal member 14 that has been bent restores its initial state, the air in the gap between the cap member 15 and the seal member 14 can be released to the outside from the introduction hole 15a.

Furthermore, according to the present embodiment, when the opening-and-closing device H is detached from the dialysate-extracting device 10, the part of the seal member 14 of the opening-and-closing device H that is on the inner side with respect to the seal portion 14a is bendable and displaceable toward the collecting port 10d by reducing the volume of the fluid (the dialysate in the present embodiment) in the dialysate flow route (the dialysate-introducing line L1) to which the dialysate-extracting device 10 is connected. Exemplary methods of reducing the volume of the fluid (dialysate) include a method in which the ultrafiltration pump 8 is activated (see FIG. 7), a method in which the pressurizing pump 9 is activated (see FIG. 8), and a method in which the duplex pump 7 serving as a fluid-delivering pump is activated (see FIGS. 9 and 10).

A case where the volume of the fluid (dialysate) is reduced by activating the ultrafiltration pump 8 will now be described with reference to FIG. 7.

First, an end c of the dialysate-introducing line L1 and an end d of the dialysate-discharging line L2 are connected to each other, the electromagnetic valves V1, V2, V4, V5, V6, and V7 are closed (the flow route is closed), the electromagnetic valve V3 is opened (the flow route is released), and the ultrafiltration pump 8 is activated. In this case, the pressurizing pump 9 and the duplex pump 7 are not in operation. Thus, the volume of the dialysate at the point of connection between the dialysate-introducing line L1 and the dialysate-extracting device 10 can be reduced, and the inner part of the seal member 14 can be bent toward the collecting port 10d. Alternatively, the pressurizing pump 9 and the duplex pump 7 may be activated. If the duplex pump 7 is activated, the electromagnetic valve V7 (or the electromagnetic valve V4) needs to be opened.

Next, a case where the volume of the fluid (dialysate) is reduced by activating the pressurizing pump 9 will be described with reference to FIG. 8.

First, the end c of the dialysate-introducing line L1 and the end d of the dialysate-discharging line L2 are connected to each other, the electromagnetic valves V1, V2, V4, V5, and V7 are closed (the flow route is closed), the electromagnetic valves V3 and V6 are opened (the flow route is released), and the pressurizing pump 9 is activated. In this case, the ultrafiltration pump 8 and the duplex pump 7 are not in operation. Thus, the volume of the dialysate at the point of connection between the dialysate-introducing line L1 and the dialysate-extracting device 10 can be reduced, and the inner part of the seal member 14 can be bent toward the collecting port 10d. Alternatively, the duplex pump 7 may be activated. In that case, the electromagnetic valve V7 (or the electromagnetic valve V4) needs to be opened.

Next, a case where the volume of the fluid (dialysate) is reduced by activating the duplex pump 7 will be described with reference to FIG. 9.

First, the end c of the dialysate-introducing line L1 and the end d of the dialysate-discharging line L2 are connected to each other, the electromagnetic valves V1, V2, V4, V5, V6, and V7 are closed (the flow route is closed), the electromagnetic valve V3 is opened (the flow route is released), and the duplex pump 7 is activated. In this case, the ultrafiltration pump 8 and the pressurizing pump 9 are not in operation. Thus, the volume of the dialysate at the point of connection between the dialysate-introducing line L1 and the dialysate-extracting device 10 can be reduced, and the inner part of the seal member 14 can be bent toward the collecting port 10d. Alternatively, the pressurizing pump 9 may be activated.

Alternatively, as illustrated in FIG. 10, a detour line L9 that detours the duplex pump 7 may be connected to the dialysate-introducing line L1, and an electromagnetic valve V8 may be provided to the detour line L9. When the duplex pump 7 is activated with the electromagnetic valve V8 being open, the dialysate flows through the detour line L9, thereby serving as a relief device. In such a case also, the volume of the dialysate at the point of connection between the dialysate-introducing line L1 and the dialysate-extracting device 10 can be reduced, and the inner part of the seal member 14 can be bent toward the collecting port 10d.

According to the above embodiment, the part on the inner side with respect to the seal portion 14a is bendable and displaceable toward the collecting port 10d when the opening-and-closing device H is detached from the dialysate-extracting device 10. Therefore, scattering of the dialysate that may occur when the opening-and-closing device H is detached from the collecting port 10d can be prevented, and the cleanliness of the collecting port 10d can be assuredly maintained. Particularly, in the present embodiment, since the part on the inner side with respect to the seal portion 14a is bent and displaced toward the collecting port 10d, the dialysate trapped in the space Y can be released into the insertion hole 10da. Therefore, spilling of the dialysate trapped in the space Y to the outside that may occur when the opening-and-closing device H is detached can be prevented.

The opening-and-closing device H according to the present embodiment includes the seal member 14 that is a flexible member, a part of which forms the seal portion 14a; and the cap member 15 that covers and holds the seal member 14. The part of the seal member 14 that is on the inner side with respect to the seal portion 14a is bendable and displaceable toward the collecting port 10d. Hence, while the sealing with the seal member 14 and the displacement of the seal member 14 are smoothly achieved, detaching and attaching the opening-and-closing device H from and to the collecting port 10d of the dialysate-extracting device 10 can be made easy by the cap member 15.

Furthermore, according to the present embodiment, when the opening-and-closing device H is detached from the dialysate-extracting device 10, the volume of the fluid (dialysate) in the dialysate flow route (the dialysate-introducing line L1) to which the dialysate-extracting device 10 is connected is reduced, whereby the part of the seal member 14 of the opening-and-closing device H that is on the inner side with respect to the seal portion 14a is bendable and displaceable toward the collecting port 10d. Thus, the seal member 14 can be assuredly bent and displaced toward the collecting port. The trigger for reducing the volume of the fluid in the dialysate flow route to which the dialysate-extracting device 10 is connected may be given by an operator operating an operation device when detaching the opening-and-closing device H or may be controlled automatically by the apparatus itself.

Now, a second embodiment of the present invention will be described.

As in the first embodiment, a dialysate-extracting apparatus according to the present embodiment is provided to a blood-purification apparatus used for blood-purification treatment (blood dialysis treatment) and can collect dialysate. The applicable blood-purification apparatus is configured as illustrated in FIG. 1. Detailed description of elements that are the same as those described in the first embodiment is omitted.

The dialysate-extracting apparatus according to the present embodiment includes a dialysate-extracting device 10 connected to a dialysate flow route (a dialysate-introducing line L1) and having a collecting port 10d from which the dialysate flowing in the dialysate flow route is collectable, and an opening-and-closing device H detachable from and attachable to the dialysate-extracting device 10 in such a manner as to open and close the collecting port 10d and including a seal portion 14a that seals the collecting port 10d in the closed state. The opening-and-closing device H includes a seal member 14 that is a flexible member, a part of which forms the seal portion 14a; and a cap member 15' that covers and holds the seal member 14.

As illustrated in FIGS. 11 and 12, the cap member 15' according to the present embodiment has a space 15'a provided between the cap member 15' and the seal member 14 and that allows the seal member 14 to be bendable and displaceable toward the collecting port 10d. Hence, when (before) the opening-and-closing device H is detached from the dialysate-extracting device 10 by elastically deforming and bending the seal member 14 that is in the state illustrated in FIG. 11, the air in the space 15'a expands. Thus, as illustrated in FIG. 12, a part on the inner side with respect to the seal portion 14a can be displaced toward the collecting port 10d.

According to the present embodiment, the cap member 15' has the space 15'a provided between the cap member 15' and the seal member 14 and that allows the seal member 14 to be bendable and displaceable toward the collecting port 10d. Hence, the seal member 14 can be bent smoothly and assuredly without providing any hole or the like in the cap member 15'. As a method of bending the seal member 14, it is preferable to reduce the volume of the fluid (dialysate) in the dialysate flow route (the dialysate-introducing line L1) to which the dialysate-extracting device 10 is connected, as described in the first embodiment.

Now, a third embodiment of the present invention will be described.

As in the first and second embodiments, a dialysate-extracting apparatus according to the present embodiment is provided to a blood-purification apparatus used for blood-purification treatment (blood dialysis treatment) and can collect dialysate. The applicable blood-purification apparatus is configured as illustrated in FIG. 1. Detailed description of elements that are the same as those described in either of the first and second embodiments is omitted.

The dialysate-extracting apparatus according to the present embodiment includes a dialysate-extracting device 10 connected to a dialysate flow route (a dialysate-introducing line L1) and having a collecting port 10d from which the dialysate flowing in the dialysate flow route is collectable, and an opening-and-closing device H detachable from and attachable to the dialysate-extracting device 10 in such a manner as to open and close the collecting port 10d and including a seal portion 14a that seals the collecting port 10d in the closed state. The opening-and-closing device H includes a seal member 14 that is a flexible member, a part of which forms the seal portion 14a; and a cap member 15" that covers and holds the seal member 14.

As illustrated in FIGS. 13 and 14, the cap member 15" according to the present embodiment has an opening 15"a through which the seal member 14 is allowed to be pushed. The seal member 14 is bendable and displaceable toward the collecting port 10d through the opening 15"a. That is, the cap member 15" has, at the top thereof, the opening 15"a into which a finger of the operator, a switch component, or the like is insertable. When (before) the opening-and-closing device H is detached from the dialysate-extracting device 10, a finger or a switch component is inserted into the opening 15"a. Thus, the seal member 14 in the state illustrated in FIG. 13 can be pushed from the back thereof, and the seal member 14 can be displaced toward the collecting port 10d as illustrated in FIG. 14.

According to the present embodiment, the cap member 15" has the opening 15"a through which the seal member 14 is allowed to be pushed, and the seal member 14 is bendable and displaceable toward the collecting port 10d through the opening 15"a. Hence, the seal member 14 can be bent and displaced toward the collecting port 10d at an arbitrary timing before the opening-and-closing device H is detached. The seal member 14 may be pushed and bent through the opening 15"a by using a finger or a switch component or by applying a positive pressure thereto through the opening 15"a.

While the embodiments have been described above, the present invention is not limited thereto. For example, the opening-and-closing device H may be any of the following: a device having none of the cap members 15, 15', and 15" but only the seal member 14; a device in which the seal portion 14a of the seal member 14 comes into contact with the top end 10db of the collecting port 10d and seals the collecting port 10d; a device including a seal member 14 having no projection 14b, and the like. While the embodiments each concern a case where the opening-and-closing device H is held by the lid member 16, the opening-and-closing device H itself may be detachable from and attachable to the collecting port 10d.

The blood-purification apparatus to which any of the embodiments is applied may be provided in any mode. For example, the blood-purification apparatus may be any of the following: an apparatus in which the dialysate is introduced or discharged by a chamber instead of the duplex pump 7, an apparatus including a blood-purification device in a mode other than the mode of the dialyzer 1, and an apparatus including neither the pressure-detecting device α nor the pressure-detecting device β or only the pressure-detecting device R. Moreover, while the embodiments each concern a case where the dialysate-extracting apparatus is provided to the dialysate-introducing line L1 of the dialysis-apparatus body B, the dialysate-extracting apparatus may be provided to another flow route located in the dialysis-apparatus body.

The present invention is applicable to any dialysate-extracting apparatus, such as an apparatus having a different outer shape, an apparatus having additional functions, or the like, as long as the dialysate-extracting apparatus includes an opening-and-closing device whose part on the inner side with respect to a seal portion is bendable and displaceable toward a collecting port when the opening-and-closing device is detached from a dialysate-extracting device.

REFERENCE SIGN LIST 1 dialyzer (blood-purification device)
2 arterial blood circuit
3 venous blood circuit
4 blood pump
5 arterial air-trapping chamber
6 venous air-trapping chamber
7 duplex pump (fluid-delivering pump)
8 ultrafiltration pump
9 pressurizing pump
10 dialysate-extracting device
11, 12 filter
13 chamber
14 seal member
15 cap member
H opening-and-closing device
α, β pressure-detecting device

The invention claimed is:

1. A dialysate-extracting apparatus comprising:
a dialysate-extracting device connected to a dialysate flow route and having a collecting port from which dialysate flowing in the dialysate flow route is collectable; and
an opening-and-closing device detachable from and attachable to the dialysate-extracting device in such a manner as to open and close the collecting port and including a seal portion that seals the collecting port in a closed state,
wherein, when the opening-and-closing device is detached from the dialysate-extracting device, a part of the opening-and-closing device that is on an inner side with respect to the seal portion is bendable and displaceable toward the collecting port.

2. The dialysate-extracting apparatus according to claim 1, wherein the opening-and-closing device includes:
a seal member that is a flexible member, a part of which forms the seal portion; and
a cap member that covers and holds the seal member, and wherein a part of the seal member that is on the inner side with respect to the seal portion is bendable and displaceable toward the collecting port.

3. The dialysate-extracting apparatus according to claim 2, wherein the cap member has an introduction hole that allows outside air to be introduced into a gap between the cap member and the seal member when the seal member is bent and displaced toward the collecting port.

4. The dialysate-extracting apparatus according to claim 2, wherein the cap member has a space provided between the cap member and the seal member and that allows the seal member to be bendable and displaceable toward the collecting port.

5. The dialysate-extracting apparatus according to claim 1, wherein, when the opening-and-closing device is detached from the dialysate-extracting device, the part of the opening-and-closing device that is on the inner side with respect to the seal portion is bendable and displaceable toward the collecting port by reducing a volume of fluid in the dialysate flow route to which the dialysate-extracting device is connected.

6. The dialysate-extracting apparatus according to claim 2, wherein the cap member has an opening through which the seal member is allowed to be pushed, and the seal member is bendable and displaceable toward the collecting port through the opening.

7. The dialysate-extracting apparatus according to claim 4, wherein, when the opening-and-closing device is detached from the dialysate-extracting device, the part of the opening-and-closing device that is on the inner side with respect to the seal portion is bendable and displaceable toward the collecting port by reducing a volume of fluid in the dialysate flow route to which the dialysate-extracting device is connected.

8. The dialysate-extracting apparatus according to claim 3, wherein, when the opening-and-closing device is detached from the dialysate-extracting device, the part of the opening-and-closing device that is on the inner side with respect to the seal portion is bendable and displaceable toward the collecting port by reducing a volume of fluid in the dialysate flow route to which the dialysate-extracting device is connected.

9. The dialysate-extracting apparatus according to claim 6, wherein, when the opening-and-closing device is detached from the dialysate-extracting device, the part of the opening-and-closing device that is on the inner side with respect to the seal portion is bendable and displaceable toward the collecting port by reducing a volume of fluid in the dialysate flow route to which the dialysate-extracting device is connected.

* * * * *